US011614394B2

(12) United States Patent
Kitaguchi

(10) Patent No.: US 11,614,394 B2
(45) Date of Patent: Mar. 28, 2023

(54) METHOD FOR ESTIMATING CHARACTERISTICS OF CERAMIC FIRED BODY

(71) Applicant: NGK INSULATORS, LTD., Nagoya (JP)

(72) Inventor: Daniel Yukichi Kitaguchi, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 574 days.

(21) Appl. No.: 16/785,994

(22) Filed: Feb. 10, 2020

(65) Prior Publication Data

US 2020/0300745 A1    Sep. 24, 2020

(30) Foreign Application Priority Data

Mar. 22, 2019    (JP) .............................. JP2019-055640

(51) Int. Cl.
*G01N 15/08*    (2006.01)
*G01N 21/25*    (2006.01)
*G01N 25/16*    (2006.01)
*G01N 33/38*    (2006.01)

(52) U.S. Cl.
CPC ........... *G01N 15/088* (2013.01); *G01N 21/25* (2013.01); *G01N 25/16* (2013.01); *G01N 33/388* (2013.01)

(58) Field of Classification Search
CPC ........ G01N 15/08; G01N 21/25; G01N 25/16; G01N 25/18; G01N 15/088; G01N 33/38; G01N 33/388; G01N 15/1434; G01N 2291/0232; G01N 21/95692; G01N 21/412

USPC .............. 427/559; 428/116, 325; 501/1, 80; 700/83; 702/19, 33, 136, 183
See application file for complete search history.

(56) References Cited

U.S. PATENT DOCUMENTS

| | | | | |
|---|---|---|---|---|
| 5,589,429 A | * | 12/1996 | Kawaguchi | C04B 35/581 264/650 |
| 6,638,885 B1 | * | 10/2003 | McGrath | C01G 23/053 423/326 |
| 2005/0217395 A1 | * | 10/2005 | Iwabuchi | G01N 15/0893 73/865.8 |
| 2011/0149462 A1 | * | 6/2011 | Kugimoto | H01L 21/6831 252/520.5 |
| 2013/0206601 A1 | * | 8/2013 | Fukuyama | C25D 11/16 356/612 |
| 2015/0367335 A1 | * | 12/2015 | Okazaki | B01J 35/10 428/116 |

FOREIGN PATENT DOCUMENTS

JP    2005-315861 A1    11/2005
WO   WO-2011118596 A1 *   9/2011   ........... C25D 11/045

* cited by examiner

*Primary Examiner* — Jeffrey P Aiello
(74) *Attorney, Agent, or Firm* — Burr Patent Law, PLLC

(57) ABSTRACT

A method for estimating characteristics of a ceramic fired body, the method including: preparing a ceramic fired body by firing a formed green body; measuring a color of the ceramic fired body; and with use of a correlation between the color and at least one characteristic selected from a group consisting of a porosity, a pore diameter, and a thermal expansion coefficient previously determined for a ceramic fired body having a same composition as that of the ceramic fired body, estimating the at least one characteristic of the ceramic fired body from the color of the ceramic fired body, measured in the previous step.

11 Claims, 13 Drawing Sheets

Exhaust Gas

METHOD FOR ESTIMATING CHARACTERISTICS OF CERAMIC FIRED BODY

FIELD OF THE INVENTION

The present invention relates to a method for estimating characteristics of a ceramic fired body.

BACKGROUND OF THE INVENTION

Ceramic products are used for various industrial applications such as heat sinks, filters, catalyst supports, sliding parts, nozzles, heat exchangers, electrical insulation members and parts for semiconductor manufacturing apparatuses, utilizing their characteristics such as high heat resistance, high hardness, high chemical resistance, and high abrasion resistance. In general, the ceramic products are produced through steps including mixing and kneading ceramic raw material powder, a dispersion medium, a binder, a pore former, and the like to form a green body, and then molding and firing the green body into a predetermined shape.

In the industrial production of ceramic products, it is desired to perform quality control by checking whether or not various characteristics required for ceramic products such as porosity, a pore diameter and a thermal expansion coefficient fulfill predetermined criteria. In recent years, higher quality has been required for the ceramic products, and importance of the quality control for satisfying the required quality has been further increased.

However, implementation of a quality inspection on all inspection items for all the produced ceramic products increases costs and delays delivery. Therefore, conventionally, in some cases, the quality control has been performed by a sampling inspection. Further, there have been circumstances where a destructive test is required for measuring the porosity, the pore diameter, and the thermal expansion coefficient, so it is difficult to inspect all products. Under such circumstances, a prior art proposes a method for easily carrying out a quality inspection of ceramic products.

Japanese Patent Application Publication No. 2005-315861 A (Patent Document 1) proposes an inspection method for a porous structure, which can be easily carried out by inspecting the weight of a formed body that has been processed into a predetermined size after forming and drying, without requiring a special device or technique, and also can easily inspect all the products. More particularly, Patent Document 1 discloses a method for inspecting a porous structure, including previously measuring a relationship between a pore characteristic of a fired body, which is obtained by firing a formed body having a predetermined shape after forming and drying, and the weight of the formed body, and setting a standard value for the pore characteristic of the fired body and a standard value for the weight of the formed body, and then inspecting the pore characteristic of the fired body from the weight of the formed body based on each of the standard values.

CITATION LIST

Patent Literature

Patent Document 1: Japanese Patent Application Publication No. 2005-315861 A

SUMMARY OF THE INVENTION

Patent Document 1 focuses on a correlation between the weight and the pore characteristic of the ceramic formed body and proposes the method for simply and non-destructively carrying out the quality inspection for the ceramic product. However, it is believed that it is also useful to provide a method for simply and non-destructively carrying out a quality inspection for a ceramic product by a method other than the weight measurement. The present invention has been made in view of the above circumstances. In one aspect, an object of the present invention is to provide a method for non-destructively estimating characteristics of a ceramic fired body without relying on weight measurement.

As a result of intensive studies to solve the above problems, the present inventor has found that the color of the fired ceramic body has a significant correlation with the porosity, the pore diameter, and the thermal expansion coefficient. The present invention has been made based on the finding, and is illustrated below.

[] A method for estimating characteristics of a ceramic fired body, the method comprising:
preparing a ceramic fired body by firing a formed green body;
measuring a color of the ceramic fired body; and
with use of a correlation between the color and at least one characteristic selected from a group consisting of a porosity, a pore diameter, and a thermal expansion coefficient previously determined for a ceramic fired body having a same composition as that of the ceramic fired body, estimating the at least one characteristic of the ceramic fired body from the color of the ceramic fired body, measured in the previous step.

[2] The method for estimating characteristics of the ceramic fired body according to [1], wherein as the correlation, a correlation having a coefficient of determination ($R^2$) of 0.7 or more for a linear regression equation is used.

[3] The method for estimating characteristics of the ceramic fired body according to [1] or [2], wherein the correlation is a correlation between the at least one characteristic and a Z component in a CIE 1931 XYZ color space.

[4] The method for estimating characteristic of the ceramic fired body according to [1] or [2], wherein the correlation is a correlation between the at least one characteristic and an L* component in a CIE 1976 (L*, a*, b*) color space.

[5] The method for estimating characteristics of the ceramic fired body according to any one of [1] to [4], wherein the at least one characteristic is the pore diameter.

[6] The method for estimating characteristics of the ceramic fired body according to any one of [1] to [5], wherein the ceramic fired body is made of cordierite.

[7] The method for estimating characteristics of the ceramic fired body according to any one of [1] to [6], wherein the ceramic fired body comprises a pillar-shaped honeycomb structure portion, the pillar-shaped honeycomb structure portion comprising: an outer peripheral side wall; and partition walls disposed on an inner peripheral side of the outer peripheral side wall, the partition walls defining a plurality of cells, each cell forming a flow path from one end face to another end face for a fluid.

[8] The method for estimating characteristics of the ceramic fired body according to [7], wherein the step of measuring the color comprises measuring a color of the one end face, and wherein as the correlation, a correlation between the at least one characteristic and the color of the one end face is used.

[9] The method for estimating characteristics of the ceramic fired body according to [8], wherein the color of the one end face is measured while shielding the other end face from light by a flat surface having a predetermined material and color.

[10] The method for estimating characteristics of the ceramic fired body according to [7], wherein the step of measuring the color comprises measuring a color of the outer peripheral side wall, and wherein as the correlation, a correlation between the at least one characteristic and the color of the outer peripheral side wall is used.

[11] A method for carrying out a quality inspection of a ceramic fired body based on the at least one characteristic estimated by the method for estimating characteristics of the ceramic fired body according to any one of [1] to [10].

According to the method for estimating characteristics of the ceramic fired body according to the present invention, one, preferably two, more preferably three characteristics selected from the group consisting of a porosity, a pore diameter and a thermal expansion coefficient of a ceramic fired body can be estimated simply by measuring a color of the ceramic fired body. Therefore, the present invention is useful, for example, as a method for easily carrying out a quality inspection for a ceramic fired body. Further, since it measures the color of the honeycomb fired body, a color tone can be managed together.

Conventionally, when measuring pore characteristics such as a pore diameter and porosity of a ceramic fired body, and a thermal expansion coefficient, a destructive test is carried out. Therefore, the sample cannot be diverted to other tests, and it takes time for the measurement. Further, the measuring sample is wasted, resulting in a decrease in yield. However, according to an embodiment of the method for estimating characteristics of the ceramic fired body according to the present invention, it is possible to estimate the pore characteristics and the thermal expansion coefficient in a short time without wasting the sample.

DETAILED DESCRIPTION OF THE INVENTION

Hereinafter, embodiments according to the present invention will be specifically described with reference to the drawings. It is to understand that the present invention is not limited to the following embodiments, and various modifications and improvements, which will be within the scope of the present invention, may be made based on ordinary knowledge of a person skilled in the art, without departing from the spirit of the present invention.

According to a method for estimating characteristics of a ceramic fired body of the present invention, the method includes:

preparing a ceramic fired body by firing a formed green body;

measuring a color of the ceramic fired body; and with use of a correlation between the color and at least one characteristic selected from the group consisting of a porosity, a pore diameter, and a thermal expansion coefficient previously determined for a ceramic fired body having the same composition as that of the ceramic fired body, estimating at least one characteristic of the ceramic fired body from the color of the ceramic fired body, measured in the previous step.

(1. Step of Preparing Ceramic Fired Body)

The ceramic fired body can be prepared by any known method. In general, the ceramic fired body can be prepared through a step of mixing and kneading ceramic raw material powder, a dispersion medium, a binder, a pore former, and the like to form a green body, and then forming the green body into a predetermined shape and firing it. A type of ceramics produced in this step is not limited. Examples of the ceramics include cordierite, mullite, zircon, aluminum titanate, silicon carbide, a silicon-silicon carbide composite, zirconia, spinel, indialite, sapphirine, corundum, titania and the like. These ceramics may be contained alone, or in combination of two or more.

However, in terms of easily recognizing a color change of the ceramic fired body, the ceramic fired body preferably has a relatively bright color. More particularly, the ceramic fired body to be measured preferably has a value (lightness) of an L* component in a CIE 1976 (L*, a*, b*) color space of preferably 30 or more, and more preferably 40 or more, and even more preferably 50 or more. An upper limit is not particularly set for the lightness, but it may generally be 90 or less, and typically 80 or less. Therefore, when it is used as an exhaust gas filter for a motor vehicle and/or a catalyst support, for example, white colored or milky white colored cordierite can be suitably used as a ceramic.

Also, an application of the ceramic fired body is not limited. As an example, a ceramic fired body used for various industrial applications such as heat sinks, filters (e.g., GPFs, DPFs), catalyst supports, sliding parts, nozzles, heat exchangers, electrical insulation members, and parts for semiconductor manufacturing apparatus can be subjected to the characteristic estimation according to the present invention.

Figure 1:
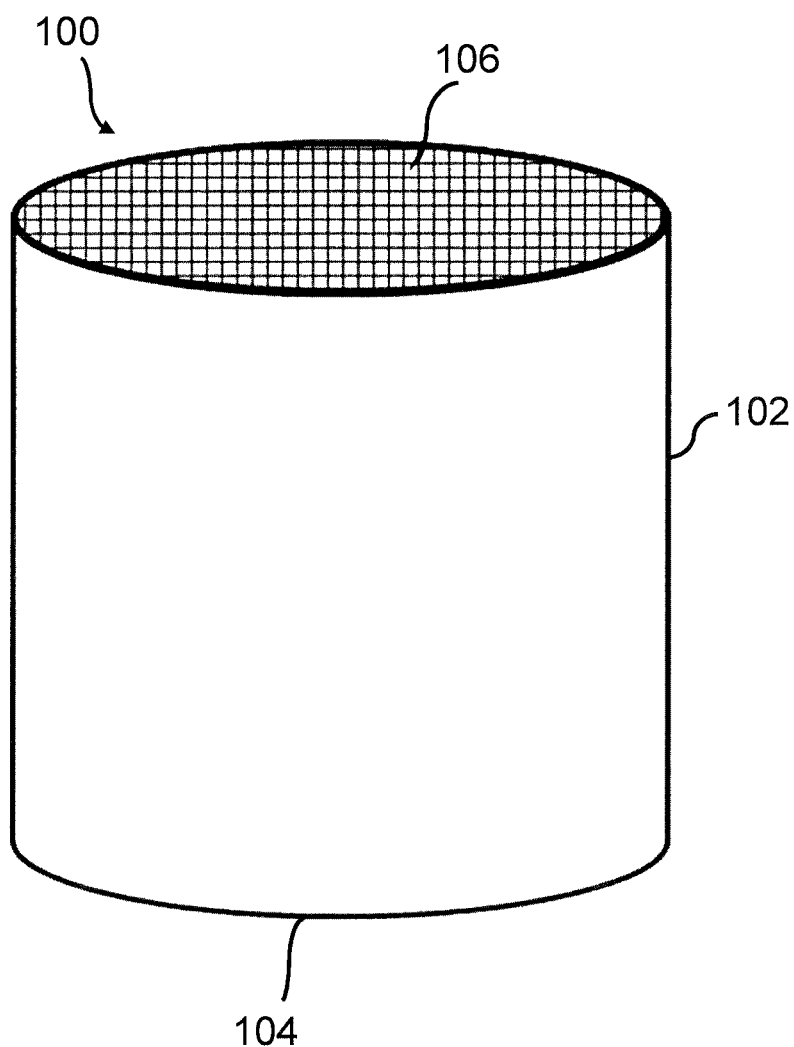
FIG. 1 is a perspective view schematically showing a wall-through type ceramic fired body.
Figure 2:
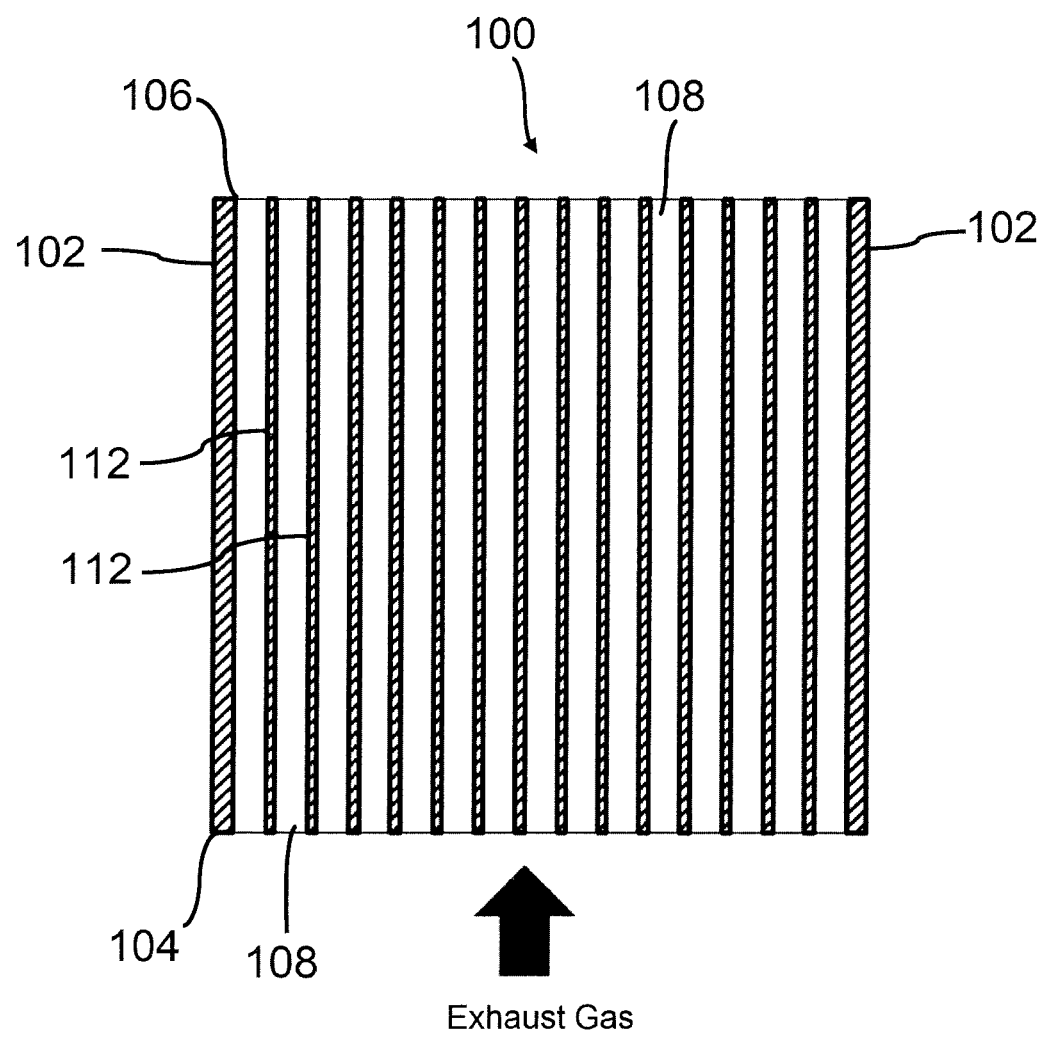
FIG. 2 is a schematic cross-sectional view of a wall-through type ceramic fired body as observed from a direction perpendicular to a cell extending direction.

FIGS. 1 and 2 respectively shows a schematic perspective view and a schematic cross-sectional view of a ceramic fired body (100) applicable as a wall-through type exhaust gas filter for a motor vehicle and/or as a catalyst support. The ceramic fired body (100) includes: an outer peripheral side wall (102); and partition walls (112) which are disposed on an inner peripheral side of the outer peripheral side wall (102) and define a plurality of cells (108) that form flow paths from one end face (104) to other end face (106) for a fluid. In this ceramic fired body (100), both ends of each cell (108) are opened, and an exhaust gas flowing into one cell (108) from one end face (104) is purified while passing through the cell, and flows out from the other end face (106).

Figure 3:
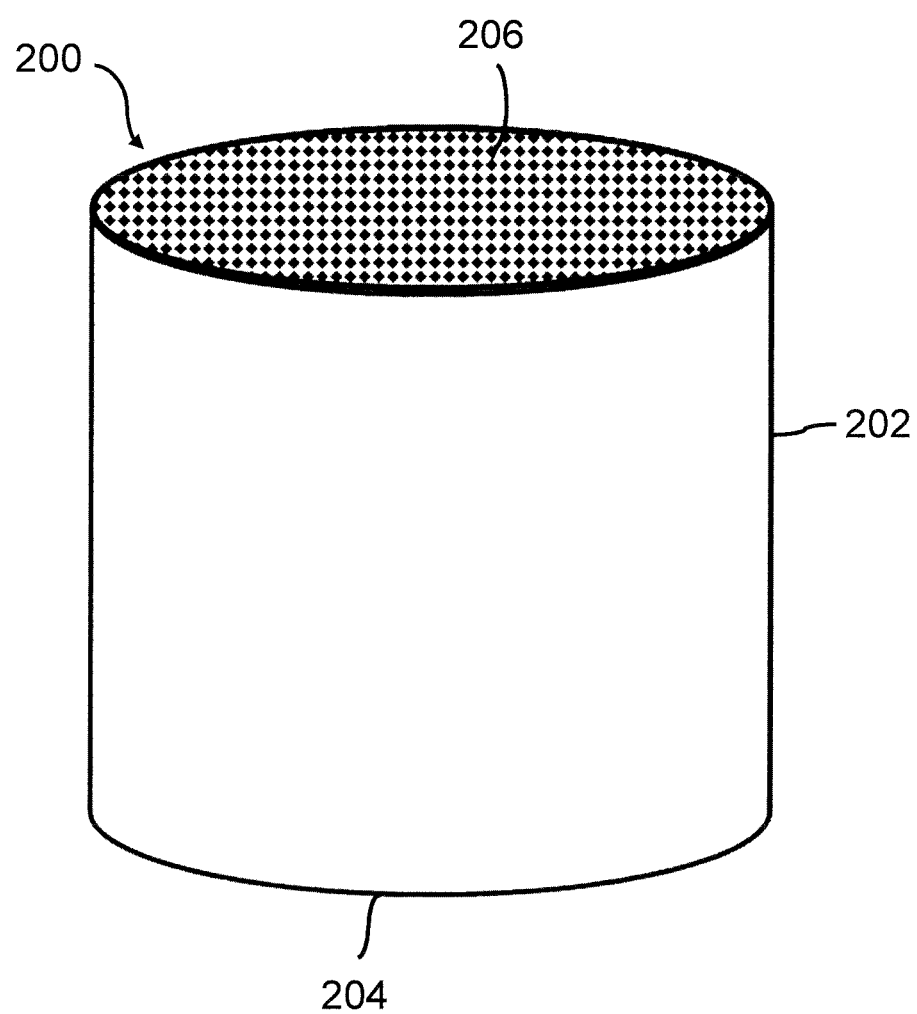
FIG. 3 is a perspective view schematically showing a wall-flow type ceramic fired body.
Figure 4:
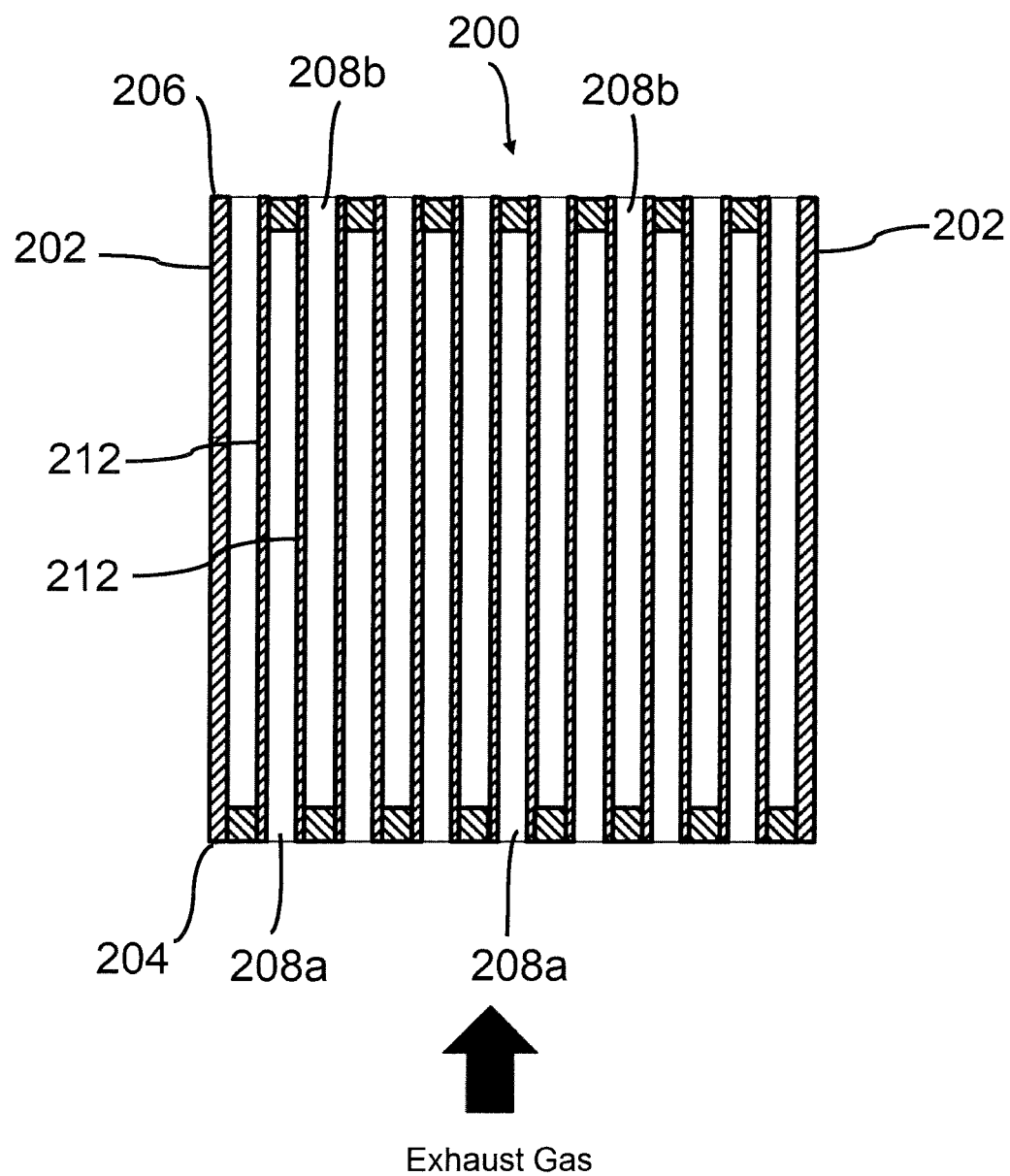
FIG. 4 is a schematic cross-sectional view of wall-flow type ceramic fired body as observed from a direction perpendicular to a cell extending direction.

FIGS. 3 and 4 respectively show a schematic perspective view and a cross-sectional view of a ceramic fired body (200) applicable as a wall-flow type exhaust gas filter for a motor vehicle and/or as a catalyst support. The ceramic fired body (200) includes: an outer peripheral side wall (202): and partition walls (212) which are disposed on an inner peripheral side of the outer peripheral side wall (202) and define a plurality of cells (208a, 208b) that form flow paths from one end face (204) to other end face (206) for a fluid.

In the ceramic fired body (200), a plurality of cells (208a, 208b) can be classified into a plurality of first cells (208a) which extend from a first end face (204) to a second end face (206) with the first end face (204) opened and the second end face (206) plugged; and a plurality of second cells (208b) which are disposed on an inner side of the outer peripheral side wall (202) and extend from the first end face (204) to the second end face (206) with the first end face (204) plugged and the second end face (206) opened. In the ceramic fired body (200), the first cell (208a) and the second cell (208b) are alternately arranged so as to be adjacent to each other across the partition wall (212).

When an exhaust gas containing soot is fed to the first end face (204) on an upstream side of the ceramic fired body (200), the exhaust gas is introduced into the first cells (208a) and flows through the first cells (208a) toward the downstream. Since the first cells (208a) are plugged on the second end face (206) on the downstream side, the exhaust gas flows through the porous partition walls (212) that define the first cells (208a) and the second cells (208b), and flows into the second cells (208b). Since the soot cannot pass through the partition walls (212), it is collected and deposited in the first cells (208a). After removing the soot, the cleaned exhaust gas that has flowed into the second cells (208b) travels in the second cells (208b) toward the downstream, and flows out from the second end face (206) on the downstream side.

Examples of an end face shape of the ceramic fired body (100, 200) includes, but not limited to, polygonal and irregular shapes such as circular, elliptical, racetrack, oval, triangular, approximately triangular, square and approximately square shapes. The illustrated ceramic fired body has a circular end face shape and a circular pillar shape as a whole.

Preferable examples of a shape of the cell in a cross section perpendicular to the cell flow path direction includes, but not limited to, a square, a hexagon, an octagon, or a combination thereof. Among these, the square and hexagon are preferred. Such a cell shape can lead to decreased pressure loss when a fluid flows through the honeycomb fired body, resulting in improved purification performance of the catalyst.

Examples of a cell density (a number of cells per unit cross-sectional area) include, but not limited to, from 6 to 2000 cells/in$^2$ (from 0.9 to 311 cells/cm$^2$), and more preferably from 50 to 1000 cells/in$^2$ (from 7.8 to 155 cell/cm$^2$), and even more preferably from 100 to 600 cells/in$^2$ (from 15.5 to 92.0 cells/cm$^2$). Here, the cell density is calculated by dividing one end face area of the ceramic fired body (100, 200) excluding the outer peripheral side wall by an opening area of the entire cell on the end face (if there are plugged cells, the calculation is carried out by determining the cells to be not plugged).

The partition walls can be porous. The porosity of the partition walls may be adjusted as needed depending on applications. It may preferably be 40% or more, and more preferably 50% or more, and even more preferably 60%, in terms of suppressing the pressure loss of the fluid. The porosity of the partition walls may preferably be 80% or less, and more preferably 75% or less, and even more preferably 70% or less, in terms of ensuring the strength of the honeycomb fired body. The porosity is measured by a mercury porosimetry using a mercury porosimeter in accordance with JIS R 1655: 2003.

It is desirable that an average pore diameter of the partition walls is set in an appropriate range depending on applications. For example, when the honeycomb fired body is used as a filter, the average pore diameter of the partition walls is preferably 24 μm or less, and more preferably 22 μm or less, and even more preferably 20 μm or less. The average pore diameter of the partition walls in the above range can result in a significantly improved collection efficiency of particulate matters. Further, the average pore diameter of the partition walls is preferably 5 μm or more, and more preferably 10 μm or more, and even more preferably 15 μm or more. The average pore diameter of the partition walls in the above range can suppress a decrease in pressure loss.

Each of the partition walls preferably has a thickness of 150 μm or more, and more preferably 170 μm or more, and even more preferably 190 μm or more, in terms of enhancing the strength of the honeycomb fired body and the collection efficiency in the case of filter use. Further, the thickness of each partition wall is preferably 260 μm or less, and more preferably 240 μm or less, and still more preferably 220 μm or less, in terms of suppressing the pressure loss.

When the ceramic fired body (100, 200) is used as a catalyst support, the surface of the partition walls (112, 212) can be coated with an appropriate catalyst depending on the purpose. Examples of the catalyst include, but not limited to, an oxidation catalyst (DOC) for oxidizing and burning hydrocarbons (HC) and carbon monoxide (CO) to increase an exhaust gas temperature; a PM combustion catalyst for assisting combustion of PMs such as soot; a SCR catalyst and NSR catalyst for removing nitrogen oxides ($NO_x$); and a three-way catalyst capable of simultaneously removing hydrocarbons (HC), carbon monoxide (CO) and nitrogen oxides ($NO_x$). The catalyst may contain, for example, noble metals (Pt, Pd, Rh, etc.), alkali metals (Li, Na, K, Cs, etc.), alkaline earth metals (Mg, Ca, Ba, Sr, etc.), rare earths (Ce, Sm, Gd, Nd, Y, La, Pr, etc.), transition metals (Mn, Fe, Co, Ni, Cu, Zn, Sc, Ti, Zr, V, Cr, etc.) and the like.

A ceramic fired body having a pillar-shaped honeycomb structure portion (hereinafter, also referred to as a "honeycomb fired body") like the ceramic fired body (100, 200) can be prepared by a known producing method, which is described below by way of example. First, a raw material composition containing a ceramic raw material, a dispersion medium, a pore former, and a binder is kneaded to form a green body, and the green body is then extruded to form a desired pillar-shaped honeycomb formed body. An additive such as a dispersant can be added to the raw material composition as needed. In the extrusion molding, a die having a desired overall shape, cell shape, partition wall thickness, cell density, and the like can be used.

The ceramic raw material is a material for a portion that remains after firing of metal oxides, metals and the like and forms a skeleton of the honeycomb fired body as ceramics. The ceramic raw material can be provided, for example, in the form of powder. Examples of the ceramic raw material include a raw material for obtaining ceramics such as cordierite, mullite, zircon, aluminum titanate, silicon carbide, silicon nitride, zirconia, spinel, indialite, sapphirine, corundum, and titania. Specific examples include, but not limited to, silica, talc, alumina, kaolin, serpentine, pyroferrite, brucite, boehmite, mullite, magnesite, and aluminum hydroxide. The ceramic raw material may be used alone or in combination of two or more.

For filter applications such as DPFs and GPFs, the cordierite can be suitably used as a ceramic. In this case, a cordierite raw material can be used as the ceramic raw material. The cordierite raw material is a raw material that forms cordierite by firing. The cordierite raw material is comprised of a chemical composition having from 30 to 45% by mass of alumina ($Al_2O_3$) (including a fraction of aluminum hydroxide converted into alumina); from 11 to 17% by mass of magnesia (MgO); and from 42 to 57% by mass of silica ($SiO_2$).

The pore former is not particularly limited as long as it forms pores after firing. Examples of the pore former include flour, starch, foaming resins, water-absorbent resins, silica gel, carbon (e.g., graphite), ceramic balloon, polyethylene, polystyrene, polypropylene, nylon, polyester, acrylic resins, phenol resins, foamed resins, and unfoamed resin. The pore former may be used alone or in combination of two or more. In terms of increasing the porosity of the honeycomb fired body, the content of the pore former is preferably 0.5 parts by mass or more, and more preferably 2 parts by mass or more, and even more preferably 3 parts by mass or more, based on 100 parts by mass of the ceramic raw material. In terms of ensuring the strength of the honeycomb fired body, the content of the pore former is preferably 10 parts by mass or less, and more preferably 7 parts by mass or less, and even more preferably 4 parts by mass or more, based on 100 parts by mass of the ceramic raw material.

Examples of the binder include organic binders such as methyl cellulose, hydroxypropylmethyl cellulose, hydroxyethyl cellulose, carboxymethyl cellulose, and polyvinyl alcohol. In particular, it is preferable to use methyl cellulose in combination with hydroxypropylmethyl cellulose. Further, the content of the binder is preferably 4 parts by mass or more, and more preferably 5 parts by mass or more, and even more preferably 6 parts by mass or more, based on 100 parts by mass of the raw material, in terms of increasing the strength of the honeycomb formed body. The content of the binder is preferably 9 parts by mass or less, and more preferably 8 parts by mass or less, and even more preferably 7 parts by mass or less, based on 100 parts by mass of the ceramic raw material, in terms of suppressing generation of cracks due to abnormal heat generation in the firing step. The binder may be used alone or in combination of two or more.

The dispersant that can be used includes ethylene glycol, dextrin, fatty acid soaps, polyetherpolyol, and the like. The dispersant may be used alone, or in combination of two or more. The content of the dispersant is preferably from 0 to 2 parts by mass based on 100 parts by mass of the ceramic raw material.

Examples of the dispersion medium include water and a mixed solvent of water and an organic solvent such as alcohol, and the like. In particular, water can be suitably used.

The water content of the honeycomb formed body before carrying out the drying step is preferably from 20 to 90 parts by mass, and more preferably from 60 to 85 parts by mass, and even more preferably from 70 to 80 parts by mass, based on 100 parts by mass of the ceramic raw material. The water content of the honeycomb formed body of 20 parts by mass or more based on 100 parts by mass of the ceramic raw material can easily provide an advantage that the quality of the honeycomb formed body is easily stabilized. The water content of the honeycomb formed body of 90 parts by mass or less based on 100 parts by mass of the ceramic raw material can lead to a reduced amount of shrinkage during drying, thereby suppressing deformation. As used herein, the water content of the honeycomb formed body refers to a value measured by a loss on drying method.

The pillar-shaped honeycomb formed body may be opened at both ends of all cells, as in the ceramic fired body (100). Further, the pillar-shaped honeycomb formed body may have a cell structure in which one end of the cells are alternately plugged, as in the case of the ceramic fired body (200). The method for plugging the end face of the pillar-shaped honeycomb formed body is not particularly limited, and it may employ a known method.

The plugged portions may be made of any material, such as, preferably ceramics, in terms of strength and heat resistance. The ceramics include a ceramic material containing at least one selected from the group consisting of cordierite, mullite, zircon, aluminum titanate, silicon carbide, silicon nitride, zirconia, spinel, indialite, sapphirine, corundum, and titania. The plugged portions are preferably made of a material containing 50% by mass or more, and more preferably made of a material containing 80% by mass or more of these ceramics in total. It is even more preferable that the plugged portions have the same material composition as that of the main body portion of the honeycomb formed body, because an expansion coefficient during firing can be the same, which leads to improvement of durability.

After drying the honeycomb formed body, degreasing and firing can be carried out to produce a honeycomb fired body. For the drying step, the degreasing step, and the firing step, known conditions may be employed depending on the material composition of the honeycomb formed body, and no particular description is required. However, specific examples are given below.

In the drying step, for example, conventionally known drying methods can be used, such as hot air drying, microwave drying, dielectric drying, reduced pressure drying, vacuum drying, and freeze drying. Among them, a combined drying method of hot air drying with microwave drying or dielectric drying is preferable because the entire formed body can be rapidly and uniformly dried. When forming the plugged portions, the plugged portions are formed on both end faces of the dried honeycomb formed body, and the plugged portions are then dried to obtain a honeycomb dried body.

A method for forming plugged portions will be exemplarily described. A plugging slurry is stored in a storage container. A mask having openings at positions corresponding to the cells where plugged portions are to be formed is then attached to one end face. The end face to which the mask has been attached is immersed in the storage container, and the openings are filled with the plugging slurry to form plugged portions. The plugged portions can also be formed on the other end face in the same manner.

Next, the degreasing step will be described. A combustion temperature of the binder is about 200° C., and a combustion temperature of the pore former is about from 300 to 100° C. Therefore, the degreasing step may be carried out by heating the honeycomb formed body at a temperature in a range of from about 200 to 1000° C. The heating time is not particularly limited, but it is typically from about 10 to 100 hours. The honeycomb formed body after the degreasing step is referred to as a calcined body.

The firing step can be carried out, for example, by heating the calcined body to 1350 to 1600° C. and maintaining it for 3 to 10 hours, although it depends on the material composition of the honeycomb formed body.

(2. Step of Measuring Color of Ceramic Fired Body)

The step of measuring the color of the ceramic fired body can be carried out using a known colorimeter, for example, a colorimeter capable of measuring various parameters of a CIE 1931 XYZ color space and/or a CIE 1976 (L*, a*, b*) color space.

In the step of measuring the color of the ceramic fired body, the step is preferably carried out so as to prevent light from entering the color measuring portion from the outside in order to improve accuracy of color measurement. A method for preventing light from entering the color measuring portion from the outside includes, for example, a method for covering the color measuring portion with a light-shielding member. As the light-shielding member, a hard (rigid) light-shielding member made of a hard plastic, ceramics, a hard rubber, wood, metal, or the like may be used, but the use of the light-shielding member made of a soft (flexible) light-shielding member made of a soft rubber, film, cloth, paper or the like further prevents light from entering the color measuring portion even if the color measuring portion of the ceramic fired body has irregularities or curved surfaces. By thus preventing light from entering the color measuring portion from the outside, only light emitted from the colorimeter falls on the color measuring portion, so that noises are eliminated and accuracy of color measurement is improved. Further, by measuring the color in a dark room, it is also possible to prevent light other than the light from the colorimeter from falling on the color measuring portion.

The color measuring portion of the ceramic fired body is not particularly limited. For example, when the ceramic fired body is a honeycomb fired body, the color of one of the end faces can be measured. In this case, it is preferable that the measurement is carried out while covering the one end face with the light-shielding member so as to prevent light from entering the color measuring portion from the outside. Further, in the case where both ends of the cells of the ceramic fired body are opened, light enters from the other opened end face when the one end face is measured. Furthermore, even if light is shielded such that light does not enter the other end face from the outside, light from the colorimeter falls on. Therefore, it is preferable to measure the color of one end face while shielding the other end face from light by a flat surface having a predetermined material and color. The light-shielding member having the flat surface can be appropriately selected from the light shielding members as described above for use. For example, it includes a method in which the honeycomb fired body is placed on a plate having a specific material and color so as to shield the lower end face, and the color of the upper end face is measured.

When the ceramic fired body is a honeycomb fired body, the color of the outer peripheral side wall can be measured. As described above, it is preferable to measure the color of the outer peripheral side wall by covering the outer peripheral side wall with a light-shielding member so as to prevent light from entering the color measuring portion from the outside.

(3. Step of Estimating Characteristics of Ceramic Fired Body)

The color of the ceramic fired body shows a significant correlation with a porosity, a pore diameter, and a thermal expansion coefficient, in particular the porosity and the pore diameter. Therefore, after measuring the color of the ceramic fired body, a correlation between the color and at least one characteristic selected from the group consisting of a porosity, a pore diameter and a thermal expansion coefficient, in particular a correlation between the color and at least one characteristic selected from the group consisting of a porosity and a pore diameter, which have been previously determined for a ceramic fired body having the same composition as that of the above ceramic fired body can be used to estimate the at least one characteristic of the ceramic fired body from the color of the ceramic fired body measured in the previous step.

The porosity and pore diameter of the ceramic fired body can be measured by a mercury porosimetry using, for example, a mercury porosimeter in accordance with JIS R 1655: 2003. The mercury porosimetry is a method in which a sample is immersed in mercury in a vacuum state and a uniform pressure is applied, and mercury is intruded into the sample while gradually increasing the pressure, and a pore diameter distribution is calculated from the pressure and a volume of mercury intruded into the pores. A typical example of the pore diameter includes an average pore diameter. In the mercury porosimetry, when the pressure is gradually increased, mercury is sequentially intruded from the pores having larger diameters, and when all the pores are finally filled with mercury, then a cumulative volume of mercury reaches counterbalance. The cumulative volume at this time is the total pore volume ($cm^3/g$), and the pore diameter at the time when 50% of the total pore volume of mercury is intruded is the average pore diameter. Also, the porosity can be determined from the total pore volume.

The thermal expansion coefficient includes a linear expansion coefficient and a volume expansion coefficient. Known methods of obtaining the linear expansion coefficient include an optical interference method, a X-ray diffraction method, a microscopic telescope method/optical scanning method, a push rod type dilatometer, a mechanical lever method, an optical lever method, an electric capacitance method, a strain gauge method, and the like, although not limited thereto. The volume expansion coefficient may also be measured by the known method.

The above characteristics may be measured by a plurality of measurement methods, respectively. However, it is preferable to measure them under the same measurement conditions as those used when previously determining the correlation between the characteristics and the color, in terms of obtaining a highly reliable estimated value.

From the viewpoint of improving accuracy of estimating characteristics of the ceramic fired body, it is preferable to use, as the above correlation, a correlation having a coefficient of determination ($R^2$) of 0.7 or more for a linear regression equation, and it is more preferable to use a correlation having a coefficient of determination ($R_2$) of 0.8 or more, and it is even more preferable to use a correlation having a coefficient of determination ($R^2$) of 0.9 or more. For example, a correlation having a coefficient of determination ($R^2$) of from 0.7 to 0.95 can be used.

The coefficient of determination ($R_2$) is a parameter representing a measure of accuracy of a regression equation, and takes a value from 0 to 1. For a certain characteristic of the ceramic fired body and a certain color parameter, it can be said that a correlation between them is high when a coefficient of determination determined by the regression equation based on the measured data is found close to 1, which makes it possible to estimate the characteristics from the color with high accuracy.

The coefficient of determination ($R^2$) is determined by the following equation:

$$R^2 = \frac{\sum_{i=1}^{n}(\hat{y}_i - \bar{y})^2}{\sum_{i=1}^{n}(y_i - \bar{y})^2} = 1 - \frac{\sum_{i=1}^{n}(y_i - \hat{y}_i)^2}{\sum_{i=1}^{n}(y_i - \bar{y})^2}$$

in which:
($x_i$, $y_i$) represents an actually measured data;
($x_i$, $\hat{y}_i$) represents a data estimated from the regression equation;
($\bar{x}$, $\bar{y}$) represents an average value determined from the entire data; and n represents the number of data.

The at least one characteristic has a high correlation with a Z component in the CIE 1931 XYZ color space. Among the characteristics, the porosity and the pore diameter have a higher correlation with the Z component in the CIE 1931 XYZ color space, and the porosity has a further higher correlation with the Z component in the CIE 1931 XYZ color space. For this reason, in a preferred embodiment, a correlation between the at least one characteristic and the Z component in the CIE 1931 XYZ color space can be used as that correlation. In a more preferred embodiment, a correlation between one or two characteristics selected from the group consisting of the porosity and the pore diameter, and the Z component in the CIE 1931 XYZ color space can be used as that correlation. In an even more preferred embodiment, a correlation between the porosity characteristic and the Z component in the CIE 1931 XYZ color space can be used as that correlation.

The at least one characteristic has a high correlation with an L* component in the CIE 1976 (L*, a*, b*) color space, too. Among the characteristics, the porosity and the pore diameter have a higher correlation with the L* component in the CIE 1976 (L*, a*, b*) color space, and the porosity is has a further higher correlation with the L* component in the CIE 1976 (L*, a*, b*) color space. For this reason, in a preferred embodiment, a correlation between the at least one characteristic and the L* component in the CIE 1976 (L*, a*, b*) color space can be used as that correlation. In a more preferred embodiment, a correlation between one or two characteristics selected from the group consisting of the porosity and the pore diameter, and the L* component in the CIE 1976 (L*, a*, b*) color space can be used as that correlation. In an even more preferred embodiment, a correlation between the porosity and the L* component in the CIE 1976 (L*, a*, b*) color space can be used as that correlation.

An example of the method for previously determining the correlation between the characteristic and the color include a method for creating a calibration curve or regression equation representing the correlation between each characteristic and the color for a ceramic fired body having the same composition as that of the ceramic fired body for estimating the at least one characteristic. From the viewpoint of improving the accuracy of characteristic estimation, it is preferable to create a calibration curve or regression equation representing the correlation between each characteristic and the color for a ceramic fired body having the same composition and the same dimensions as those of the ceramic fired body for estimating the at least one characteristic. By using the created calibration curve or regression equation, each characteristic can be estimated based on the color of the honeycomb fired body. Examples of the regression equation that can be used include a linear regression equation, an exponential regression equation, a logarithmic regression equation, or a polynomial regression equation, and the like. When estimating characteristics using the regression equation, it is preferable to use a regression equation having a coefficient of determination ($R^2$) of 0.7 or more, and more preferably 0.8 or more, and even more preferably 0.9 or more.

(4. Quality Inspection)

According to an embodiment of the present invention, there is provided a method for carrying out a quality inspection of a ceramic fired body based on the at least one characteristic estimated by the method for estimating characteristics as described above. That is, whether or not the estimated value of each of the above characteristics passes a predetermined criterion can be used as a criterion for the quality inspection without actually measuring each of the above characteristics.

The color of the ceramic fired body can be used for estimation of product characteristics such as dimensions, water absorption, isostatic strength, thermal shock resistance or collection efficiency, or material characteristics such as an amount of crystal, a softening temperature or stability at elevated temperature, or production condition management such as a firing temperature or a firing shrinkage rate, although it has not been described in detail herein.

EXAMPLES (1. Preparation of Honeycomb Fired Body)

To 100 parts by mass of a cordierite forming raw material were added 13 parts by mass of a pore former, 35 parts by mass of a dispersion medium, 6 parts by mass of an organic binder, and 0.5 parts by mass of a dispersant. They were mixed and kneaded to prepare a green body. As the cordierite forming raw material, alumina, aluminum hydroxide, kaolin, talc, and silica were used. Water was used as the dispersion medium, coke having an average particle diameter of from 1 to 10 pm was used as the pore former, hydroxypropylmethyl cellulose was used as the organic binder, and ethylene glycol was used as the dispersant.

The green body was placed in an extruder and extruded to obtain a cylindrical honeycomb formed body. The resulting honeycomb formed body was dried by means of dielectric drying and hot air drying, and both end faces were then cut so as to have a predetermined size to obtain a required number of honeycomb dried bodies for the following tests.

Specifications of the honeycomb dried bodies are as follows: Overall shape: cylindrical shape having a diameter of 118 mm and a height of 152 mm; Cell shape in a cross section perpendicular to a flow path direction of cells: square; Cell density (the number of cells per unit cross-sectional area): 300 cells/cm2; and Partition wall thickness: 8 mil (200 μm).

Each honeycomb dried body was then fired in an air atmosphere at various firing temperatures to obtain a large number of honeycomb fired bodies.

(2. Measurement of Color)

Each honeycomb fired body was placed on a plate (color: black, material: soft rubber) so as to shield the lower end face. Then, using a handheld colorimeter (model: NR-12A) available from NIPPON DENSHOKU INDUSTRIES Co., Ltd., the color of the upper end face of each honeycomb fired body was measured based on the CIE 1931 XYZ color space and the CIE 1976 (L*, a*, b*) color space. In the color measurement, the color measuring portion on the upper end face was light-shielded by a cover so as to prevent light other than the light source of the colorimeter from entering the color measuring portion on the upper end face from the outside.

(3. Correlation between Porosity and Color)

The porosity of the partition walls of the various honeycomb fired bodies subjected to the color measurement was measured by mercury porosimetry using a mercury porosimeter in accordance with JIS R 1655: 2003.

Figure 5:
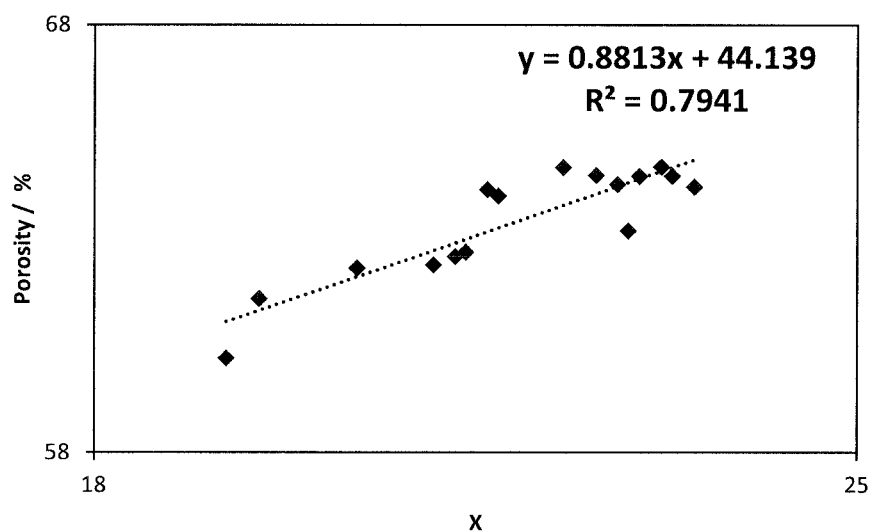
FIG. 5 shows results of plotting a relationship between an X value in a CIE 1931 XYZ color space and a porosity for each honeycomb fired body, together with a linear regression equation by a least squares method and a coefficient of determination ($R^2$).

FIG. 5 shows results of plotting a relationship between the X value (x axis) in the CIE 1931 XYZ color space and the porosity (y axis) for each honeycomb fired body, together with the linear regression equation by the least squares method and the coefficient of determination ($R^2$).

Figure 6:
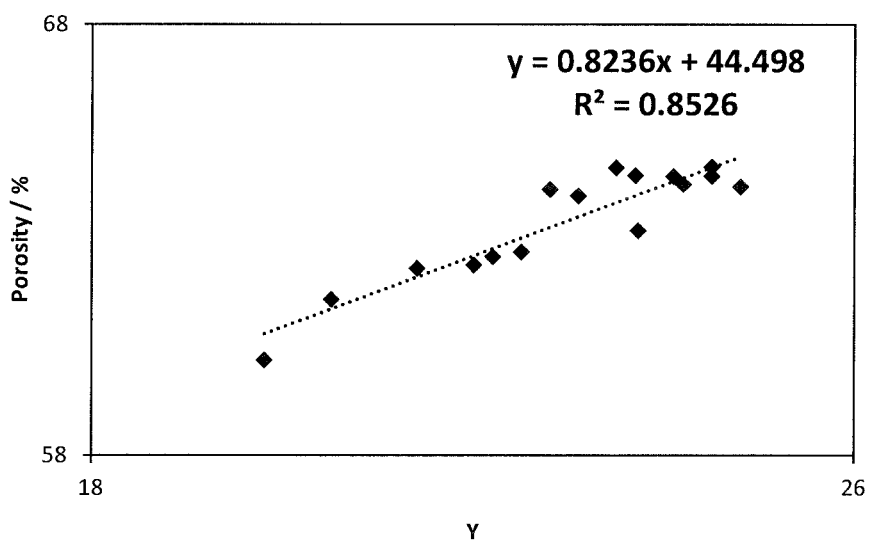
FIG. 6 shows results of plotting a relationship between a Y value in a CIE 1931 XYZ color space and a porosity for each honeycomb fired body, together with a linear regression equation by a least squares method and a coefficient of determination ($R^2$).

FIG. 6 shows results of plotting a relationship between the Y value (x axis) in the CIE 1931 XYZ color space and the porosity (y axis) for each honeycomb fired body, together with the linear regression equation by the least squares method and the coefficient of determination ($R^2$).

Figure 7:
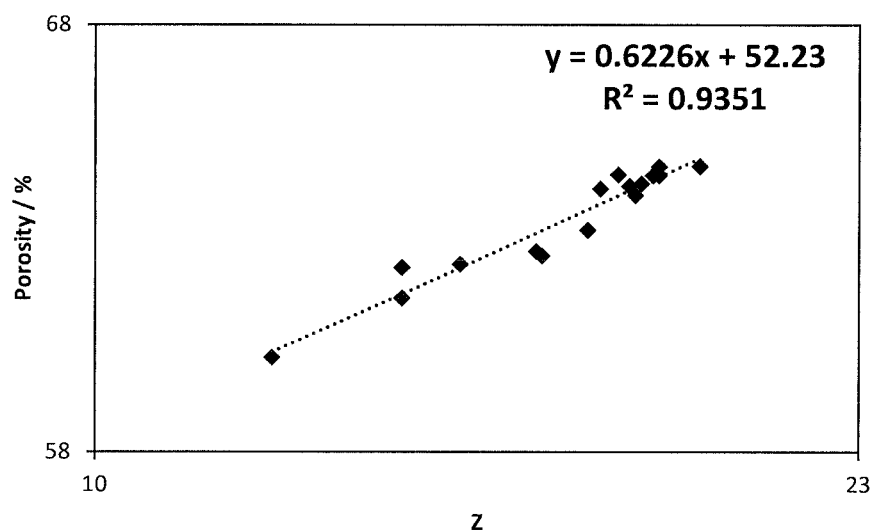
FIG. 7 shows results of plotting a relationship between a Z value in a CIE 1931 XYZ color space and a porosity for each honeycomb fired body, together with a linear regression equation by a least squares method and a coefficient of determination ($R^2$).

FIG. 7 shows results of plotting a relationship between the Z value (x axis) in the CIE 1931 XYZ color space and the porosity (y axis) for each honeycomb fired body, together with the linear regression equation by the least squares method and the coefficient of determination ($R^2$).

Figure 8:
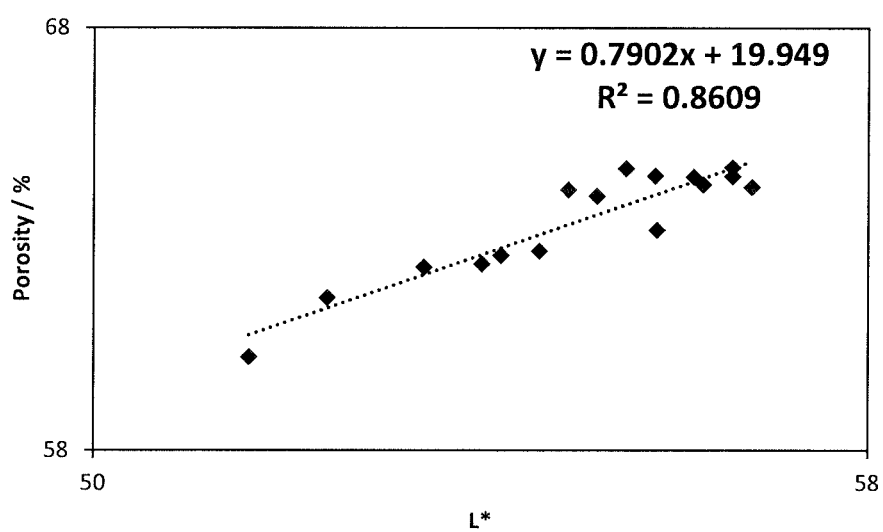
FIG. 8 shows results of plotting a relationship between an L* value in a CIE 1976 (L*, a*, b*) color space and a porosity for each honeycomb fired body, together with a linear regression equation by a least squares method and a coefficient of determination ($R^2$).

FIG. 8 shows results of plotting a relationship between the L* value (x axis) in the CIE 1976 (L*, a*, b*) color space and the porosity (y axis) for each honeycomb fired body, together with the linear regression equation by the least squares method and the coefficient of determination ($R^2$).

Figure 9:
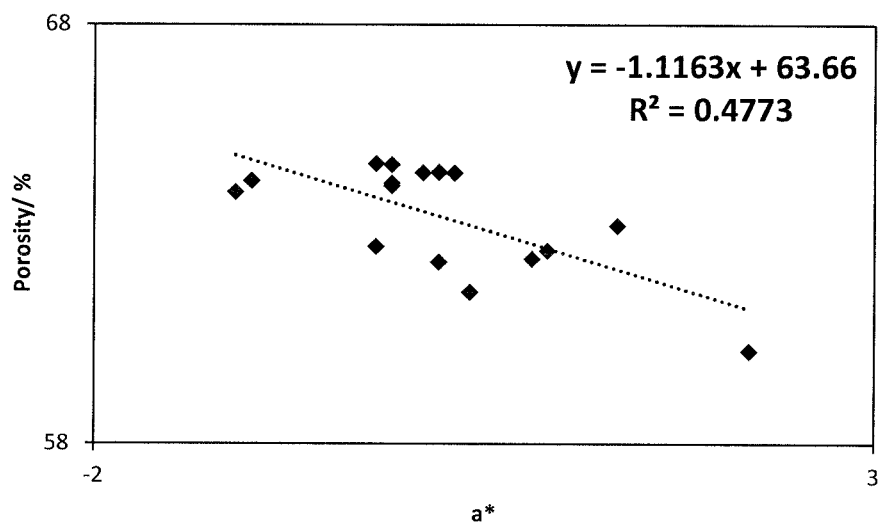
FIG. 9 shows results of plotting a relationship between an a* value in a CIE 1976 (L*, a*, b*) color space and a porosity for each honeycomb fired body, together with a linear regression equation by a least squares method and a coefficient of determination ($R^2$).

FIG. 9 shows result of plotting a relationship between the a* value (x axis) in the CIE 1976 (L*, a*, b*) color space and the porosity (y axis) for each honeycomb fired body, together with the linear regression equation by the least squares method and the coefficient of determination ($R^2$).

Figure 10:
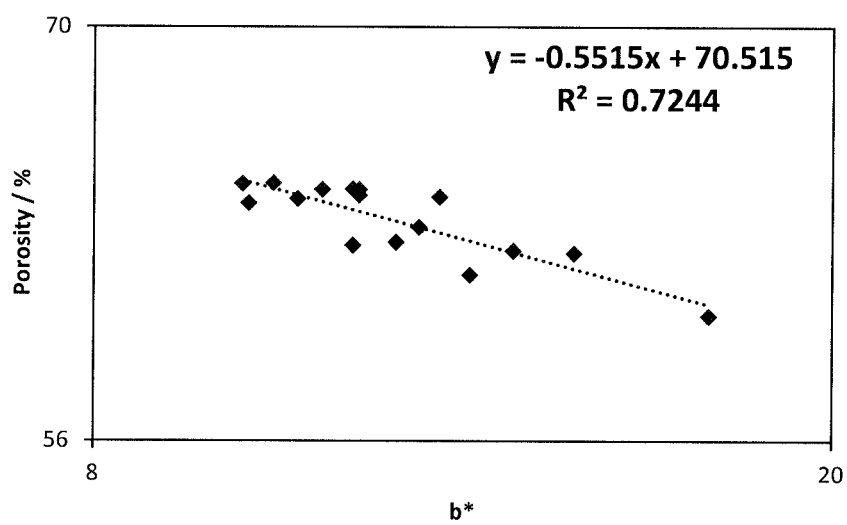
FIG. 10 shows results of plotting a relationship between a b* value in a CIE 1976 (L*, a*, b*) color space and a porosity for each honeycomb fired body, together with a linear regression equation by a least squares method and a coefficient of determination (R2).

FIG. 10 shows results of plotting a relationship between the b* value (x axis) in the CIE 1976 (L*, a*, b*) color space and the porosity (y axis) for each honeycomb fired body, together with the linear regression equation by the least squares method and the coefficient of determination ($R^2$).

The above results show that the porosity can be estimated based on the color of the honeycomb fired body, because the porosity and the color have a correlation. In particular, the coefficient of determination ($R^2$) between the Z value in the CIE 1931XYZ color space and the porosity is 0.9 or more, indicating a higher correlation.

(4. Correlation between Average Pore Diameter and Color)

The average pore diameter of the partition walls of each honeycomb fired body subjected to the color measurement was measured by a mercury porosimetry using a mercury porosimeter in accordance with JIS R 1655: 2003.

Figure 11:
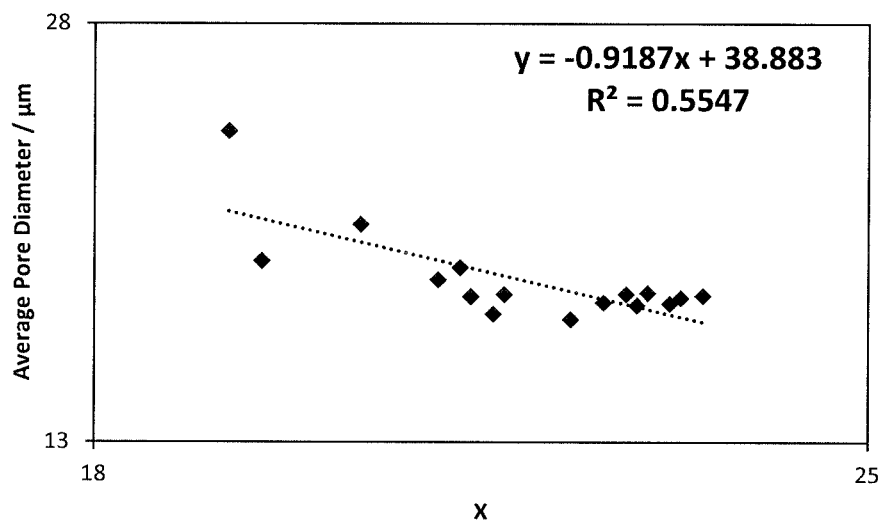
FIG. 11 shows results of plotting a relationship between an X value in a CIE 1931 XYZ color space and an average pore diameter for each honeycomb fired body, together with a linear regression equation by a least squares method and a coefficient of determination ($R^2$).

FIG. 11 shows results of plotting a relationship between the X value (x axis) in the CIE 1931 XYZ color space and the average pore diameter (y axis) for each honeycomb fired body, together with the linear regression equation by the least squares method and the coefficient of determination ($R^2$).

Figure 12:
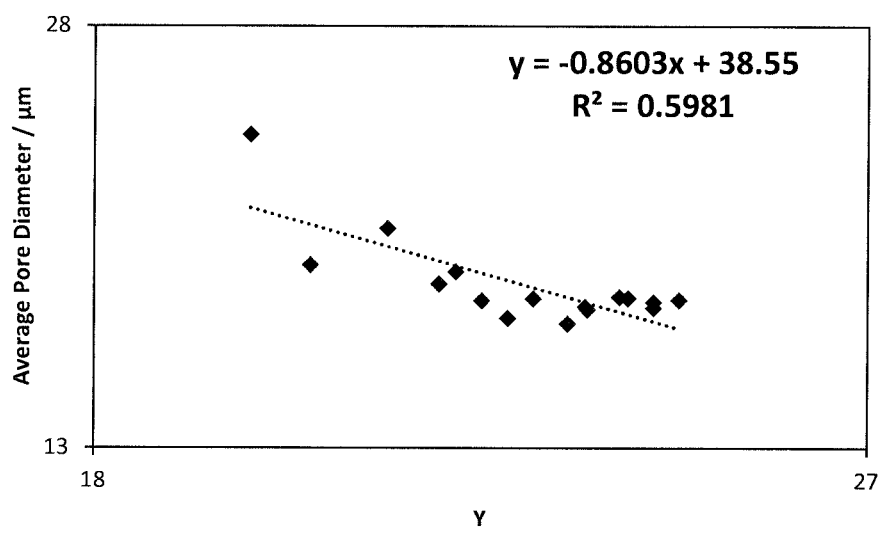
FIG. 12 shows results of plotting a relationship between a Y value in a CIE 1931 XYZ color space and an average pore diameter for each honeycomb fired body, together with a linear regression equation by a least squares method and a coefficient of determination ($R^2$).

FIG. 12 shows results of plotting a relationship between the Y value (x axis) in the CIE 1931 XYZ color space and the average pore diameter (y axis) for each honeycomb fired body, together with the linear regression equation by the least squares method and the coefficient of determination ($R^2$).

Figure 13:
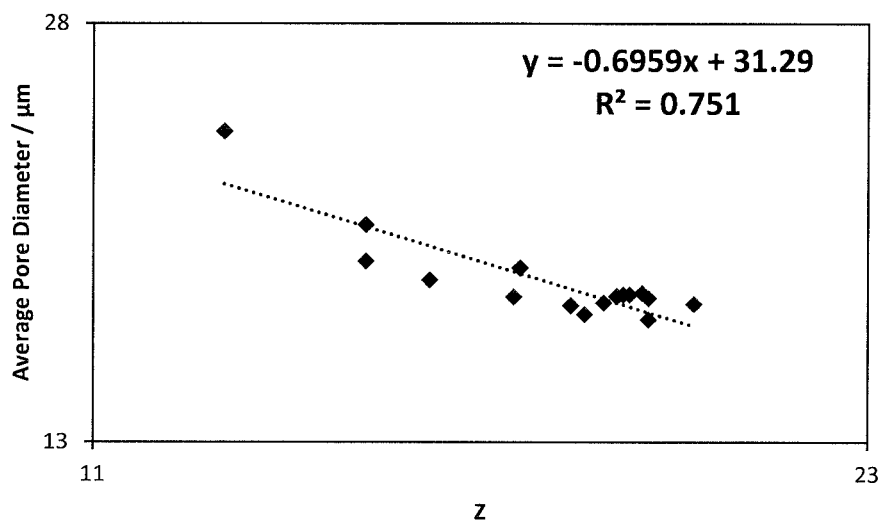
FIG. 13 shows results of plotting a relationship between a Z value in a CIE 1931 XYZ color space and an average pore diameter for each honeycomb fired body, together with a linear regression equation by a least squares method and a coefficient of determination ($R^2$).

FIG. 13 shows results of plotting a relationship between the Z value (x axis) in the CIE 1931 XYZ color space and the average pore diameter (y axis) for each honeycomb fired body, together with the linear regression equation by the least squares method and the coefficient of determination ($R^2$).

Figure 14:
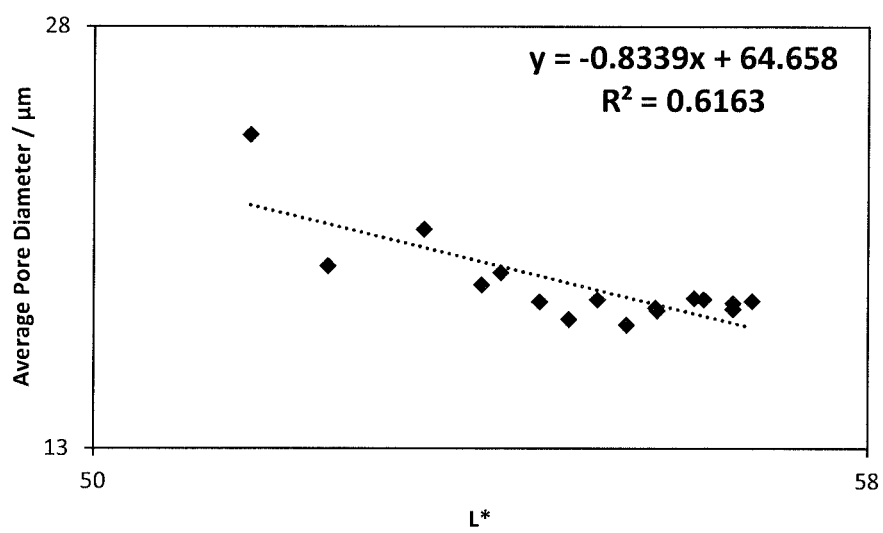
FIG. 14 shows results of plotting a relationship between a L* value in a CIE 1976 (L*, a*, b*) color space and an average pore diameter for each honeycomb fired body, together with a linear regression equation by a least squares method and a coefficient of determination ($R^2$).

FIG. 14 shows results of plotting a relationship between the L* value (x axis) in the CIE 1976 (L*, a*, b*) color space and the average pore diameter (y axis) for each honeycomb fired body, together with the linear regression equation by the least squares method and the coefficient of determination ($R^2$).

Figure 15:
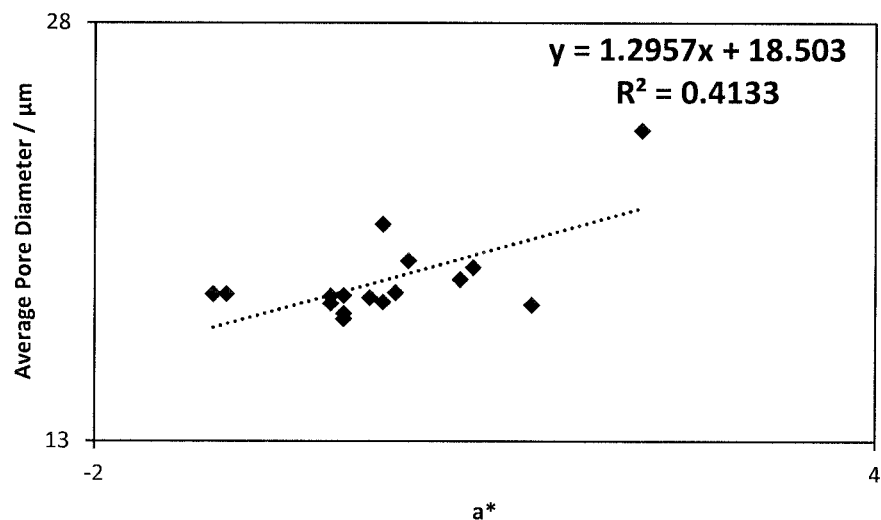
FIG. 15 shows results of plotting a relationship between an a* value in a CIE 1976 (L*, a*, b*) color space and an average pore diameter for each honeycomb fired body, together with a linear regression equation by a least squares method and a coefficient of determination ($R^2$).

FIG. 15 shows results of plotting a relationship between the a* value (x axis) in the CIE 1976 (L*, a*, b*) color space and the average pore diameter (y axis) for each honeycomb fired body, together with the linear regression equation by the least squares method and the coefficient of determination ($R^2$).

Figure 16:
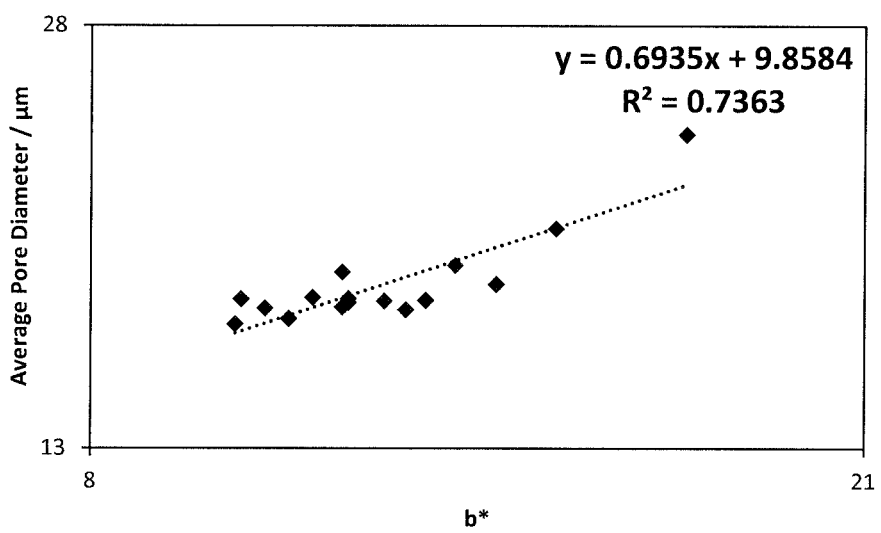
FIG. 16 shows results of plotting a relationship between a b* value in a CIE1976 (L*, a*, b*) color space and an average pore diameter for each honeycomb fired body, together with a linear regression equation by a least squares method and a coefficient of determination ($R^2$).

FIG. 16 shows results of plotting a relationship between the b* value (x axis) in the CIE 1976 (L*, a*, b*) color space and the average pore diameter (y axis) for each honeycomb fired body, together with the linear regression equation by the least squares method and the coefficient of determination ($R^2$).

The above results show that the average pore diameter can be estimated based on the color of the honeycomb fired body, because the average pore diameter and the color have a correlation. In particular, the coefficient of determination ($R^2$) between the Z value in the CIE 1931 XYZ color space and the average pore diameter is 0.7 or more, indicating a higher correlation.

(5. Correlation Between Thermal Expansion Coefficient and Color)

The thermal expansion coefficients (linear expansion coefficients) of the partition walls of the various honeycomb fired bodies subjected to the color measurement were determined by the following procedure. Each honeycomb fired body was cut out to prepare a measurement sample having a height of 5 mm, a width of 5 mm, and a length of 50 mm. The measurement sample was prepared by cutting it out from the honeycomb fired body such that the extending direction of the cells of the honeycomb fired body was the length direction of the measurement sample. The average linear expansion coefficient in the length direction when the prepared measurement sample was heated from 40° C. to 800° C. was measured by a differential detection type thermal dilatometer.

Figure 17:
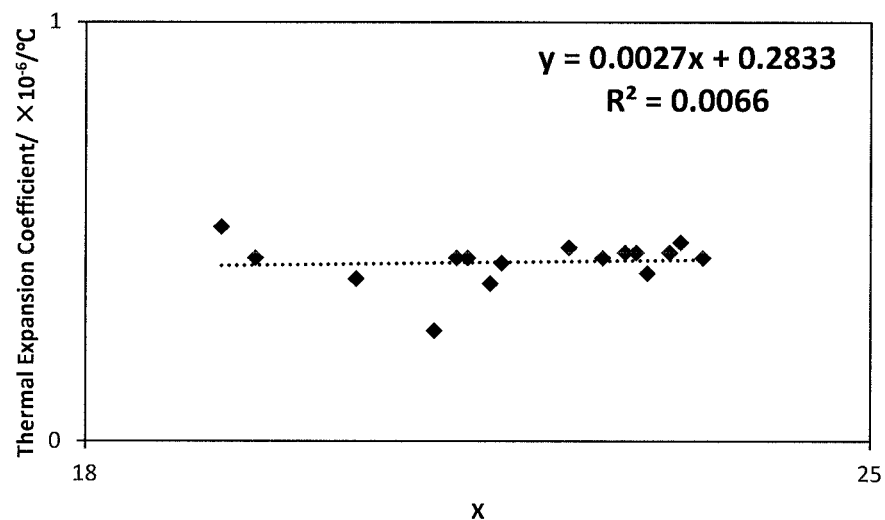
FIG. 17 shows results of plotting a relationship between an X value in a CIE 1931 XYZ color space and a thermal expansion coefficient for each honeycomb fired body, together with a linear regression equation by a least squares method and a coefficient of determination ($R_2$).

FIG. 17 shows results of plotting a relationship between the X value (x axis) in the CIE 1931 XYZ color space and the thermal expansion coefficient (y axis) for each honeycomb fired body, together with the linear regression equation by the least squares method and the coefficient of determination ($R_2$).

Figure 18:
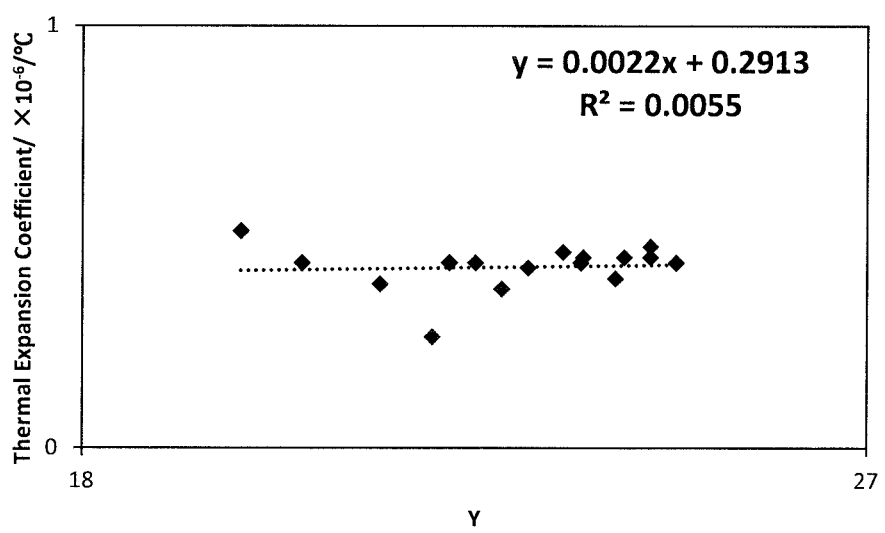
FIG. 18 shows results of plotting a relationship between a Y value in a CIE 1931 XYZ color space and a thermal expansion coefficient for each honeycomb fired body, together with a linear regression equation by a least squares method and a coefficient of determination ($R_2$).

FIG. 18 shows results of plotting a relationship between the Y value (x axis) in the CIE 1931 XYZ color space and the thermal expansion coefficient (y axis) for each honeycomb fired body, together with the linear regression equation by the least squares method and the coefficient of determination ($R_2$).

Figure 19:
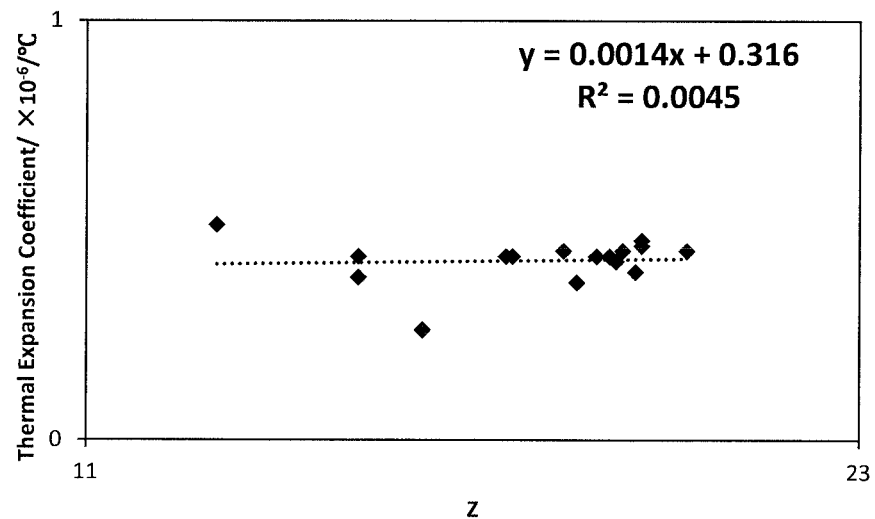
FIG. 19 shows results of plotting a relationship between a Z value in a CIE 1931 XYZ color space and a thermal expansion coefficient for each honeycomb fired body, together with a linear regression equation by a least squares method and a coefficient of determination ($R_2$).

FIG. 19 shows results of plotting a relationship between the Z value (x axis) in the CIE 1931 XYZ color space and the thermal expansion coefficient (y axis) for each honeycomb fired body, together with the linear regression equation by the least squares method and the coefficient of determination ($R_2$).

Figure 20:
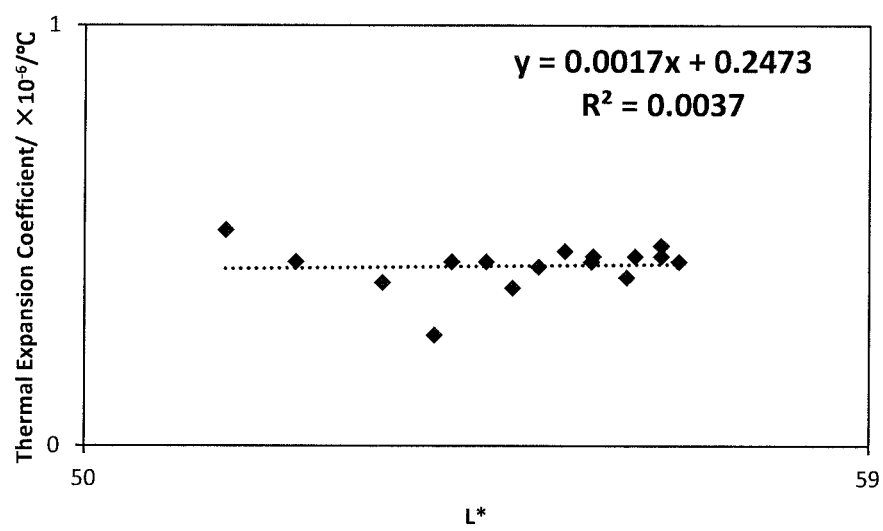
FIG. 20 shows results of plotting a relationship between an L* value in a CIE 1976 (L*, a*, b*) color space and a thermal expansion coefficient for each honeycomb fired body, together with a linear regression equation by a least squares method and a coefficient of determination ($R_2$).

FIG. 20 shows results of plotting a relationship between the L* value (x axis) in the CIE 1976 (L*, a*, b*) color space and the thermal expansion coefficient (y axis) for each honeycomb fired body, together with the linear regression equation by the least squares method and the coefficient of determination ($R_2$).

Figure 21:
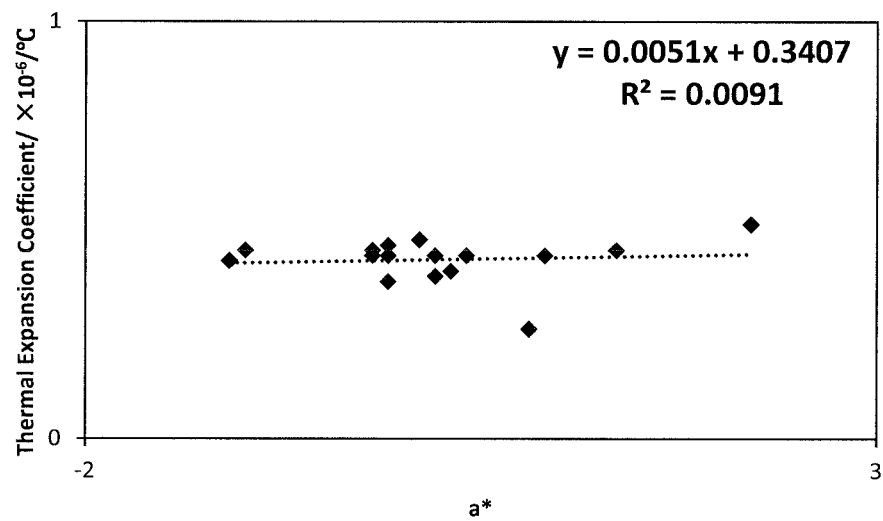
FIG. 21 shows results of plotting a relationship between an a* value in a CIE 1976 (L*, a*, b*) color space and a thermal expansion coefficient for each honeycomb fired body, together with ae linear regression equation by a least squares method and a coefficient of determination ($R_2$).

FIG. 21 shows results of plotting a relationship between the a* value (x axis) in the CIE 1976 (L*, a*, b*) color space and the thermal expansion coefficient (y axis) for each honeycomb fired body, together with the linear regression equation by the least squares method and the coefficient of determination ($R_2$).

Figure 22:
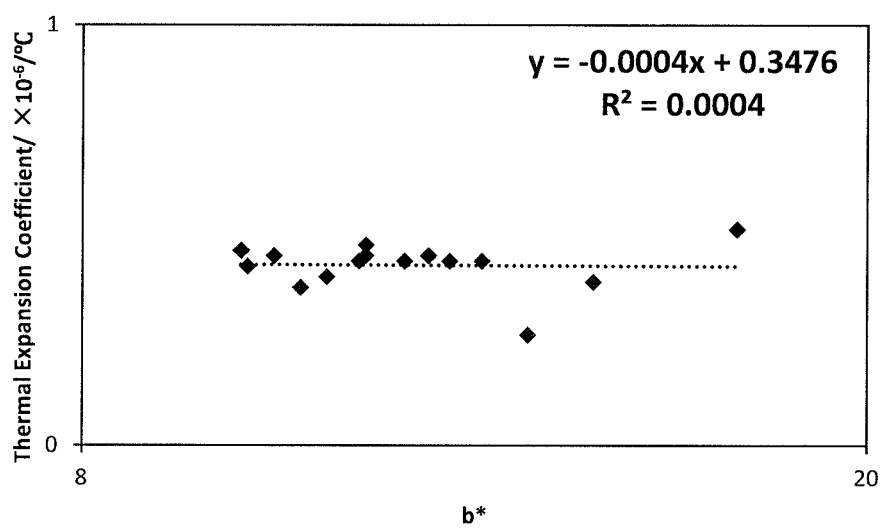
FIG. 22 shows results of plotting a relationship between a b* value in a CIE 1976 (L*, a*, b*) color space and a thermal expansion coefficient for each honeycomb fired body, together with a linear regression equation by a least squares method and a coefficient of determination ($R_2$).

FIG. 22 shows results of plotting a relationship between the b* value (x axis) in the CIE 1976 (L*, a*, b*) color space and the thermal expansion coefficient (y axis) for each honeycomb fired body, together with the linear regression equation by the least squares method and the coefficient of determination ($R_2$).

The above results show that the thermal expansion coefficient can be estimated based on the color of the honeycomb fired body, because the thermal expansion coefficient and the color have a correlation.

DESCRIPTION OF REFERENCE NUMERALS 100, 200 ceramic fired body
102, 202 outer peripheral side wall
104, 204 one end face
106, 206 the other end face
108, 208a, 208b cell
112, 212 partition wall

The invention claimed is:

1. A method for estimating characteristics of a ceramic fired body, the method comprising:
preparing a ceramic fired body by firing a formed green body;
measuring a color of the ceramic fired body; and
with use of a correlation between the color and at least one characteristic selected from a group consisting of a porosity, a pore diameter, and a thermal expansion coefficient previously determined for a ceramic fired body having a same composition as that of the ceramic fired body, estimating the at least one characteristic of the ceramic fired body from the color of the ceramic fired body, measured in the previous step.

2. The method for estimating characteristics of the ceramic fired body according to claim 1, wherein as the correlation, a correlation having a coefficient of determination ($R^2$) of 0.7 or more for a linear regression equation is used.

3. The method for estimating characteristics of the ceramic fired body according to claim 1, wherein the correlation is a correlation between the at least one characteristic and a Z component in a CIE 1931 XYZ color space.

4. The method for estimating characteristic of the ceramic fired body according to claim 1, wherein the correlation is a correlation between the at least one characteristic and an L* component in a CIE 1976 (L*, a*, b*) color space.

5. The method for estimating characteristics of the ceramic fired body according to claim 1, wherein the at least one characteristic is the pore diameter.

6. The method for estimating characteristics of the ceramic fired body according to claim 1, wherein the ceramic fired body is made of cordierite.

7. The method for estimating characteristics of the ceramic fired body according to claim 1, wherein the ceramic fired body comprises a pillar-shaped honeycomb structure portion, the pillar-shaped honeycomb structure portion comprising: an outer peripheral side wall; and partition walls disposed on an inner peripheral side of the outer peripheral side wall, the partition walls defining a plurality of cells, each cell forming a flow path from one end face to another end face for a fluid.

8. The method for estimating characteristics of the ceramic fired body according to claim 7, wherein the step of measuring the color comprises measuring a color of the one end face, and wherein as the correlation, a correlation between the at least one characteristic and the color of the one end face is used.

9. The method for estimating characteristics of the ceramic fired body according to claim 8, wherein the color of the one end face is measured while shielding the other end face from light by a flat surface having a predetermined material and color.

10. The method for estimating characteristics of the ceramic fired body according to claim 7, wherein the step of measuring the color comprises measuring a color of the outer peripheral side wall, and wherein as the correlation, a correlation between the at least one characteristic and the color of the outer peripheral side wall is used.

11. A method for carrying out a quality inspection of a ceramic fired body based on the at least one characteristic estimated by the method for estimating characteristics of the ceramic fired body according to claim 1.

* * * * *